United States Patent [19]

Bader et al.

[11] Patent Number: 4,855,111
[45] Date of Patent: Aug. 8, 1989

[54] REACTOR FOR METHANE CONVERSION

[75] Inventors: Robert A. Bader, Overbrook Hills; Michael G. Axelrod, Media, both of Pa.

[73] Assignee: Atlantic Richfield Company, Los Angeles, Calif.

[21] Appl. No.: 184,925

[22] Filed: Apr. 25, 1988

[51] Int. Cl.$^4$ .............................. B01J 8/18; B01J 8/04
[52] U.S. Cl. .................................... 422/142; 422/191; 422/195; 422/218
[58] Field of Search ............... 422/141, 142, 213, 218, 422/220, 239, 145, 147, 191, 195

[56] References Cited

U.S. PATENT DOCUMENTS

| | | | |
|---|---|---|---|
| 2,369,478 | 4/1941 | Mekler et al. | 23/288 |
| 2,425,098 | 8/1947 | Kassel | 196/52 |
| 2,632,692 | 3/1953 | Korin et al. | 23/288 |
| 2,891,846 | 6/1959 | Knight | 23/284 |
| 3,226,204 | 12/1965 | Stotler et al. | 23/284 |
| 3,793,444 | 2/1974 | Reeves et al. | 423/138 |
| 3,890,439 | 9/1976 | Mayer | 23/284 |

OTHER PUBLICATIONS

Overcashier et al.; AICHE Journal; vol. 5, No. 1, pp. 54–60, Mar. 1959.

Primary Examiner—Barry S. Richman
Assistant Examiner—D. John Griffith, Jr.
Attorney, Agent, or Firm—William C. Long

[57] ABSTRACT

The invention relates to a reactor for the conversion of methane to higher molecular weight hydrocarbons comprising an annular reaction zone with ceramic baffles positioned therein perpendicular to the flow of the mixture of gas and fluidized solid catalyst, the baffles having openings adapted to permit passage of the gas-solid mixture therethrough essentially only in the overall direction of flow from inlet to outlet.

3 Claims, 3 Drawing Sheets

REACTOR FOR METHANE CONVERSION

BACKGROUND OF THE INVENTION

1. Field of the Invention

The present invention relates to an apparatus for the conversion of methane to higher boiling hydrocarbons. In particular, the invention relates to a novel baffled reactor having adequate structural strength at elevated reaction temperatures and which is especially adapted for the use of fluidized solid catalyst systems in the conversion of methane to higher molecular weight hydrocarbons.

2. Description of the Prior Art

Methane is found in large quantities in gaseous form in somewhat remote regions of the world. The transportation of this methane to areas where it can be utilized is relatively inefficient.

Considerable work has been carried out relating to the conversion of methane to higher molecular weight hydrocarbons which are readily condensable and which can be conveniently transported in liquid form. In this regard, reference is made to the following U.S. patents which are concerned with conversion of methane to higher hydrocarbons: U.S. Pat. Nos. 4,443,649; 4,444,984; 4,443,648; 4,443,645; 4,443,647; 4,443,644; 4,443,646; 4,499,323; 4,499,324; 4,593,139; 4,489,215; 4,499,322; 4,495,374; 4,544,784; 4,544,785; 4,547,610; 4,547,611; 4,517,398; 4,544,787; 4,547,608; 4,544,786; 4,568,785; 4,523,049; 4,523,050 and the like.

The conversion of methane to higher molecular weight hydrocarbons in the presence of solids which may contain oxidative synthesizing agents as described in the above patents takes place effectively at elevated temperatures in the range of about 5000° C. to 1200° C. The reaction is strongly exothermic in nature, and in order to properly regulate the reaction and prevent excessive undesirable side reactions, it is necessary to remove the exothermic heat of reaction to avoid an excessive temperature rise, and rapidly lower the temperature of the reaction product mixture.

Problems particular to this conversion of methane include the fact that the reaction temperature is high enough to preclude or bring into serious question the use of many materials normally used in reactor construction.

Fixed bed reactors of the tubular or massive bed configuration have been considered for the reaction. However, such systems have not been satisfactory due to their cost and complexity, to pressure drop and materials of construction problems and to problems of heat removal and effluent quenching. Reference is made, however, to copending U.S. patent application Ser. No. 07/031,496 which discloses an improved thin bed monolithic reactor.

Fluidized solid reactor systems have been considered for the conversion of methane to higher molecular weight hydrocarbons. However, in conventional equipment severe problems of gas and solids backmixing and gas bypassing with resulting selectivity and yield losses have been encountered. Also structural problems are encountered which are compounded by the extreme reaction conditions which are employed and the heat resistant materials which are, of necessity, employed.

SUMMARY OF THE INVENTION

In accordance with the present invention there is provided an improved reactor design for conversion of methane to higher molecular weight hydrocarbons.

The improved reactor is comprised of an annular reaction zone having inlet and outlet means for the introduction and removal of a mixture of gases and fluidized solid catalyst particles. Positioned within the reaction zone perpendicular to the path of the mixture of gases and fluidized solid particles are a plurality of supported baffles made of ceramic material such as alumina which has appropriate structural strength at the high temperatures employed in the methane conversion reaction. The baffles, in turn, have a plurality of openings therethrough adapted to permit passage of the mixture of gases and fluidized solid particles substantially only in the overall direction of flow from inlet to outlet and thus to prevent, to a large degree, backmixing of gases and solids and gas bypassing within the reaction zone.

Preferred additional features which will be described hereinafter include particular support configuration, the provision of wedge shaped elements which make up each baffle, the provision of gas-solid separation means as well as catalyst regeneration means where appropriate.

BRIEF DESCRIPTION OF THE DRAWINGS

The accompanying drawings illustrate the invention.

Accompanying

Accompanying

Accompanying

DETAILED DESCRIPTION OF THE INVENTION

The present invention is advantageously applicable to processes of the "redox" type where methane is contacted with a reducible metal oxide in the substantial absence of gaseous oxidant and the reduced metal oxide is regenerated in a separate oxidizing step, as well as to processes of the "cofeed" type where gaseous oxidant is incorporated with methane in the gaseous feed to the reaction system.

In one practice, methane is converted to higher molecular weight hydrocarbons by contact at reactive conditions with fluidized particles of solid comprising a reducible metal oxide oxidative synthesizing agent. This contact can be carried out in the "redox" mode wherein methane is contacted with the reducible oxide in the absence of added gaseous oxidant and subsequently the reduced oxide is oxidized by contact with oxidant gas in the substantial absence of methane. See, for example, U.S. Pat. Nos. 4,443,649, 4,444,984, 4,445,648, 4,443,645, 4,443,674, 4,443,646, 4,499,323, 4,499,324 and 4,593,139 for an extensive description of this mode of operation.

Alternatively, the invention can be practiced by contacting a mixture of methane and gaseous oxidant at reactive conditions with the fluidized particles of contact solid in the "cofeed" mode of the invention. In this case, as further described below, the contact solid may comprise a reducible metal oxide oxidative synthesizing agent component or it may comprise a non acidic solid with or without the additional presence of reducible metal oxide.

Figure 1:
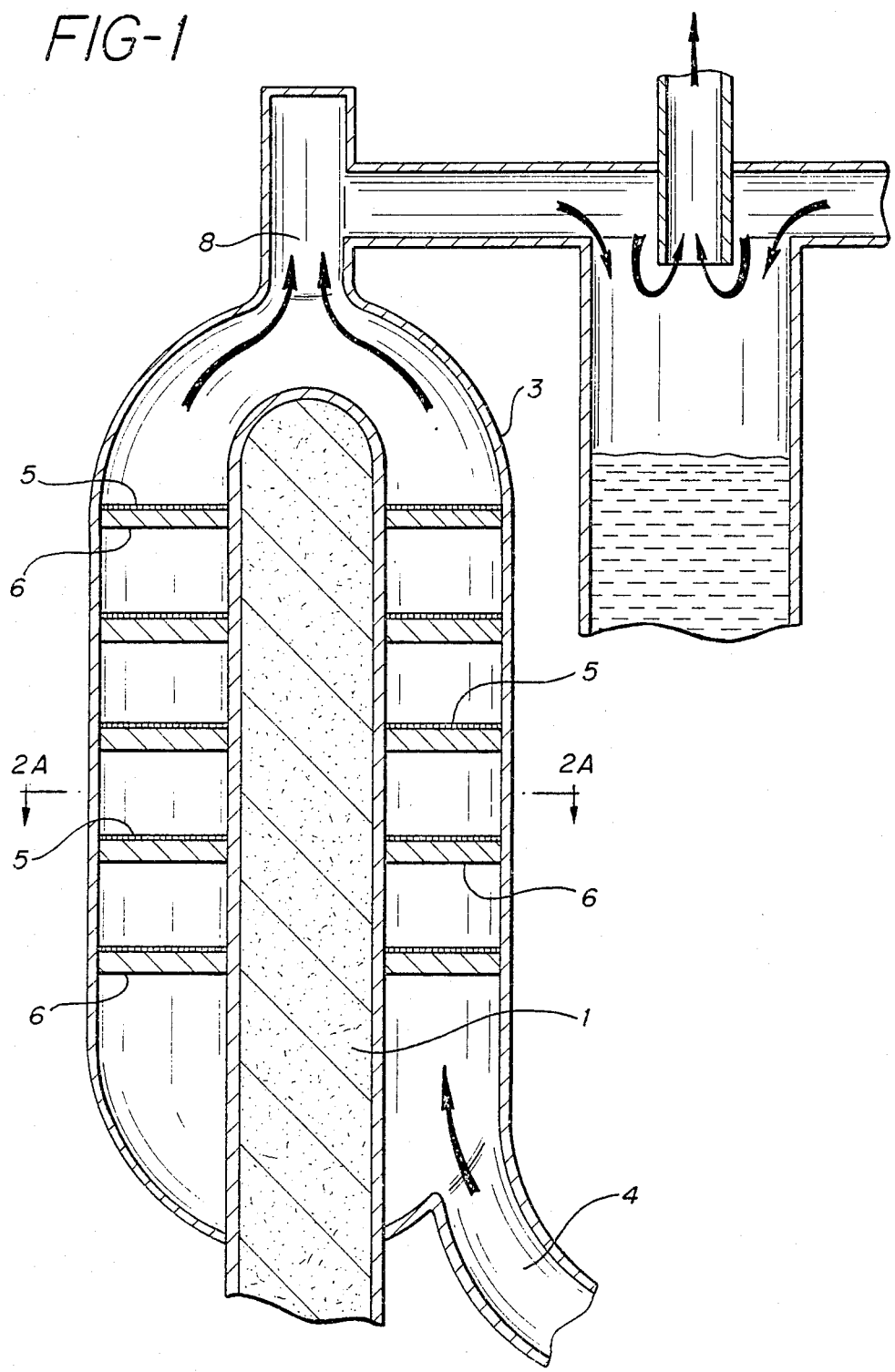
FIG. 1 is a sectional view of a reactor of the invention.

In accordance with the invention the methane conversion is carried out in a novel annular baffled reactor. Attached FIG. 1 illustrates a preferred reactor design of the invention. Referring to FIG. 1, the improved reactor comprises an inner support element 1, preferably cylindrical in shape, having a surface 2 of ceramic material which contacts the reaction mixture. Appropriately, element 1 is a steel reinforced ceramic central column which retains strength at th high temperatures of methane conversion. Cylindrical ceramic lined steel shell 3 defines the annular reaction zone in which the methane conversion takes place.

Inlet means 4 are provided through which the mixture of gas and fluidized solids is introduced into the reaction zone.

Essential to the reactor of this invention is the provision of a plurality of ceramic baffles 5 which, as shown in FIG. 1, are positioned perpendicular to the flow of the gas-fluidized solids mixture. Baffles 5, in turn, have a plurality of openings 6 which are sized to permit the passage therethrough of the gas-solids mixture.

Element 7 represents a primary distribution grid which is also formed of ceramic material which is stable at reaction conditions. Finally, outlet means 8 are provided through which the reaction mixture of gases and fluidized solids exits the reaction zone. The preferred ceramic material is comprised predominantly of alumina and may contain minor amounts of oxides of silica, calcium, and the like. In general, known ceramic materials having sufficient strength at the elevated temperatures necessary for methane conversion can be employed.

Figure 2A:
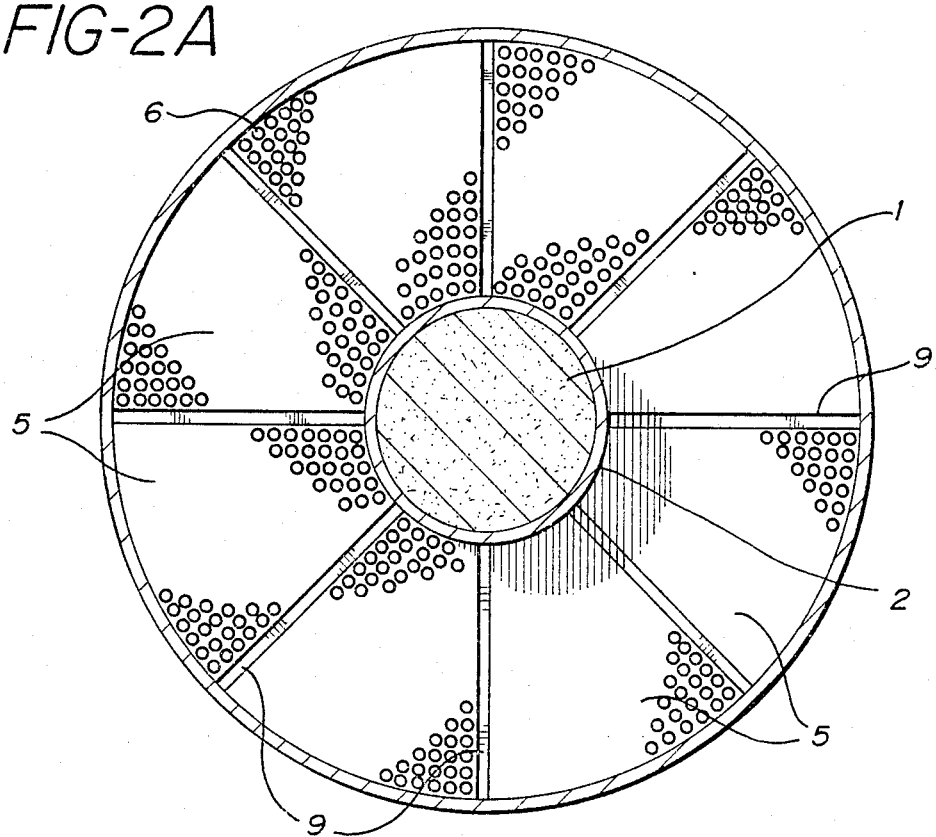
FIG. 2 is a top view of the reactor.

FIG. 2A is a top view of a section of the reactor and shows in more detail the baffles and preferred supporting means. Elements common to FIG. 1 and FIG. 2A have the same numbering.

Referring to FIG. 2A, the ceramic baffles 5 are each comprised of wedge shaped sections for ease of assembly and installation. In FIG. 2A each baffle consists of 8 sections, although this number is not critical and can be greater or lesser.

As shown in FIG. 2A the baffle sections have a plurality of openings 6 to permit passage of the gas-fluidized solid mixture therethrough. The size and number of these openings will depend on the reaction conditions and catalyst which is employed in the methane conversion. Generally, the openings should not comprise more than about 70% of the baffle area in order to provide proper structural strength, while the openings should not comprise too low a percentage or excessive pressure drop results. The opening area is generally 10–70%, preferably 15–30% of the baffle area and opening diameters of 0.25 to 3 inches are suitable.

In the preferred practice shown in FIG. 2A, ceramic support beams 9 are provided to support the baffle sections. These support beams are preferably staggered in orientation from baffle to baffle to provide uniform gas/solid contacting above the baffles.

Figure 2B:
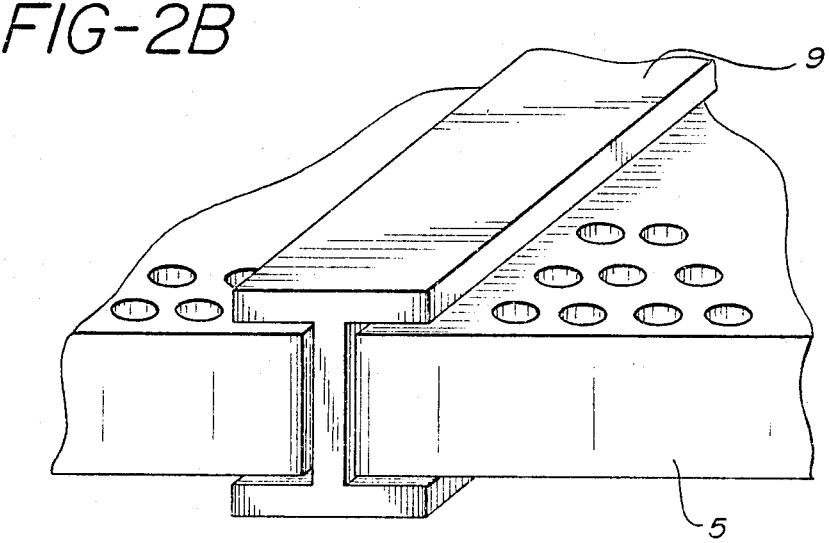

In a preferred practice, the support beams are I shaped and are welded at the ends to the outer wall of cylinder 1 and the inner wall of shell 3. Preferably, the beams are ceramic coated. A baffle section 5 is inserted into the support beam 9 as shown in FIG. 2B and thus held securely in place. In order to insert the last section of a baffle, a two section support beam is used; the lower section is first secured in place, the baffle section is positioned and the upper support beam then secured as by welding at the ends.

In addition to the provision of support beams 9, the baffles can be supported at the inner wall of outer shell 3 and at the outer wall of central column 1 on ring sections welded thereto.

Without the provision of support column 1, the construction of relatively large diameter reactors would not be practical. The baffles have considerable weight and are used at severe reaction conditions. Excessive distances between support points, therefor, are not acceptable. The support configuration shown in FIGS. 2A and 2B provides support beams between baffle sections and at the outer surface of Column 1 and the inner surface of shell 3, thereby enabling construction of structurally sound and economically large sized reactors.

In especially preferred practice, a plurality of reactors are provided in parallel with common means for distributing the gas-fluidized solid catalyst mixture, and common means for collecting and further treatment of the exit reaction mixture.

The mixture of reaction products, which includes higher molecular weight hydrocarbons, passes from the reaction zone to a separation zone for the separation of solid catalyst particles from gaseous materials. In the case where the methane conversion is carried out in the "redox" mode, it is necessary to reoxidize the oxygen depleted catalyst prior to reuse in the methane conversion reaction.

In the case of "cofeed" operation wherein gaseous oxygen is a reactive component of the methane conversion reaction mixture, a separate regeneration zone is not required.

Figure 3:
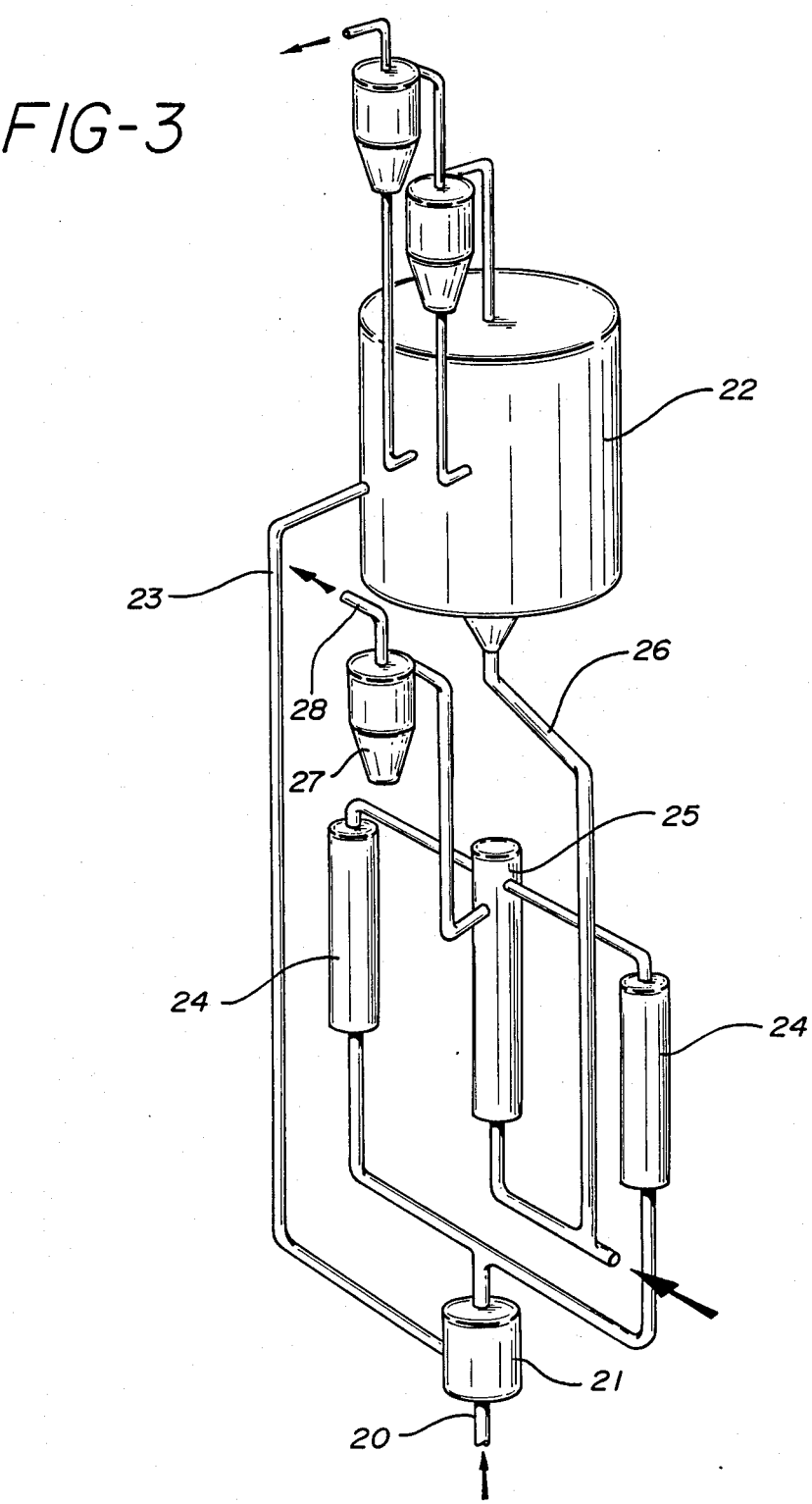
FIG. 3 illustrates a preferred overall arrangement incorporating the reactor.

FIG. 3 illustrates an overall configuration wherein methane is converted to higher hydrocarbons in a "redox mode" reaction using the reaction system of the invention.

Referring to FIG. 3, methane feed gas passes via line 20 to distributor 21 wherein the methane is combined with the solid catalyst particles returning from regeneration zone 22 by means of line 23.

From distributor 21, the mixture of methane and catalyst is distributed to the inlet means of a plurality of reactors 24 in parallel. Although, for convenience two reactors are illustrated in FIG. 3, it is generally preferred to use four or more reactors in parallel. Each reactor is as shown in FIGS. 1, 2A and 2B, and has an 11.5 ft inner diameter ceramic shell 3 and a 4 ft outer diameter inner steel reinforced ceramic central column 1. The reactors each have five baffle stages 5 which are spaced 3 feet apart. Each baffle stage is comprised of eight wedge shaped sections as shown in FIG. 2A, supported by ceramic beams 9 and at the outer wall of the inner column and the inner wall of the outer cylinder. Each baffle stage has 1255 openings of 2 inch diameter therethrough, the openings comprising about 30% of the baffle area.

The gas-fluidized solid mixture passes from inlet to outlet through the baffles while undergoing conversion of methane to higher molecular weight hydrocarbons in each reactor. The reaction product mixture exits each reactor via outlet means 8 and passes to a common central standpipe separating means 25. Disengagement of solids and gases takes place in separator 25, the solid particles passing downwardly to air riser 26 where they are conveyed in a current of air to regenerator 22. In regenerator 22 the particles which had been depleted in oxygen are reoxidized and pass back to distributor 21 via line 23.

Product gases from separator 25 pass to cyclone separator 27 wherein the separation of reaction gases from the solid particles is completed. Product gases are recovered by line 28 while solid particles are returned by means not shown to the distributor 21.

In an especially suitable practice of the invention, the regenerator is positioned above a plurality of reactors such that the supporting structure associated with the reactors in turn provides support for the regenerator. For example, where four reactors are used with a common regenerator, the reactors are geometrically positioned so that the regenerator can be centrally located above the reactors and be supported by the structures such as girders, foundations, and the like associated with the reactors.

The reactor design of this invention has a number of important advantages. It can be readily scaled up from experimental to commercial size. The reactor can be shop fabricated and assembled and disassembled quite readily. Inexpensive elements such as ceramic lined steel shells can be used with minimum duplication of peripheral equipment. The center support configuration provides adequate structural strength for the baffle elements even in large diameter reactors. The ceramic baffles, unlike metal baffles are highly resistant to erosion and thus can be employed for extended periods without replacement.

Through use of the reactor, catalyst and gas back mixing and gas bypassing ar Ⓡminimized. Rapid disengagement of catalyst from product gas to avoid unwanted side reactions can be achieved.

It is especially preferred to employ several reactors in parallel with a common disengager and regenerator in order to minimize capital costs.

In addition to the advantages enumerated above over metal baffled reactors, tests have demonstrated that the reactor of this invention provides distinct advantages when compared to operation in a non-baffled reactor.

For example, comparative tests were performed for the conversion of methane in the redox mode in a ceramic baffled reactor according to this invention and a corresponding reactor without baffles. The oxidative synthesizing agent in both cases was the same, a mixed oxide oxidative synthesizing agent having the atom ratio Li/B/Mn/Mg of 0.5/0.5/1/2.5.

When methane was oxidatively coupled by contact at 825° C. with the oxidative synthesizing agent in the baffled reactor of the invention, at methane conversion of about 20%, selectivities to higher molecular weight hydrocarbons of about 71% were obtained. In contrast under similar conditions but in a non-baffled reactor, at a 20% methane conversion substantially lower selectivity to higher molecular weight hydrocarbons, about 56% was obtained thus demonstrating the important advantages of the invention.

What is claimed is:

1. A reactor adapted for the conversion of methane to higher molecular weight hydrocarbons comprising a central support column and an outer shell which together define an annular reaction zone, inlet means for introducing a mixture of methane containing gas and fluidized solid catalyst particles into said reaction zone, outlet means for withdrawing a mixture of gas and fluidized solid catalyst particles from said zone, and a plurality of vertically spaced ceramic baffle assemblies comprised of wedged-shaped segments positioned in said reaction zone each perpendicular to said central support column and said outer shell, said baffle assemblies filling the annular cross-section between said support column and said outer shell and being supported at the outer wall of the central support column and at the inner wall of the outer shell, adjacent baffle assembly segments also being supported by radial ceramic support beams, said baffle assemblies each having a plurality of openings 0.25 to 3 inches in diameter adapted to permit passage of the mixture of gas and fluidized solid catalyst particles through said baffle assemblies only toward said outlet means, the area of said openings being 10–70% of the baffle area of each baffle assembly.

2. The reactor of claim 1 wherein said ceramic beams are staggered in orientation from baffle to baffle.

3. The reactor of claim 1 wherein the area of said openings is 15–30% of said baffle area.

* * * * *